United States Patent [19]

Patsidis et al.

[11] Patent Number: 5,393,911

[45] Date of Patent: * Feb. 28, 1995

[54] CYCLOPENTADIENE TYPE COMPOUNDS AND METHOD FOR MAKING

[75] Inventors: Konstantinos Patsidis, Bayreuth, Germany; Syriac J. Palackal, Bartlesville, Okla.; Helmut G. Alt, Bayreuth, Germany

[73] Assignee: Phillips Petroleum Company, Bartlesville, Okla.

[ * ] Notice: The portion of the term of this patent subsequent to Mar. 2, 2010 has been disclaimed.

[21] Appl. No.: 984,054

[22] Filed: Nov. 30, 1992

Related U.S. Application Data

[63] Continuation-in-part of Ser. No. 697,363, May 7, 1991, Pat. No. 5,191,132.

[51] Int. Cl.$^6$ .......................... C07F 7/08; C07C 13/28
[52] U.S. Cl. ........................... 556/489; 585/317; 585/360; 585/375; 585/376; 556/465; 556/478
[58] Field of Search ............... 585/375, 376, 317, 446, 585/360; 502/158, 232; 556/465, 478, 489

[56] References Cited

U.S. PATENT DOCUMENTS

| | | | |
|---|---|---|---|
| 3,426,069 | 2/1969 | Fritz et al. | 260/562 |
| 4,794,096 | 12/1988 | Ewen | 502/117 |
| 4,808,561 | 2/1989 | Welborn, Jr. | 502/104 |
| 4,892,851 | 1/1990 | Ewen et al. | 502/104 |
| 4,931,417 | 6/1990 | Miya et al. | 502/117 |
| 5,017,714 | 5/1991 | Welborn, Jr. | 556/12 |
| 5,049,535 | 9/1991 | Resconi et al. | 502/117 |
| 5,071,808 | 12/1991 | Antberg et al. | 502/107 |
| 5,087,677 | 2/1992 | Brekner et al. | 526/160 |
| 5,120,867 | 6/1992 | Welborn, Jr. | 556/12 |
| 5,132,381 | 7/1992 | Winter et al. | 526/160 |
| 5,145,819 | 9/1992 | Winter et al. | 502/117 |
| 5,225,501 | 7/1993 | Fujita et al. | 526/127 |

FOREIGN PATENT DOCUMENTS 0485821 5/1992 European Pat. Off. .
0485823 5/1992 European Pat. Off. .

OTHER PUBLICATIONS

Eabonn et al, 'Ultra-Violet Absorption Spectra of 9-substituted fluorenes', J. Chem. Soc., 76, pp. 2027–2030 (1954).
Darton et al, 'Unexpected Chemistry in an Attempted Generation of a Sterically Hindered Silene', J. Organometal. Chem., 172 pp. 11–19 (1979).
Chem Abs., 51:11271c (1957).
Chem. Abs., 99: 105383z (1983).
Chem. Abs., 118: 102.044q (1993).
Chem. Abs., 119: 271957r (1993).
Chem. Abs., 119:203635j.
Journal of the American Chemical Society, vol. 95, No. 5, Mar. 7, 1973, pp. 1503–1508.
Journal of the American Chemical Society, vol. 78, 1956, pp. 3530–3533.
Inorganic Chemistry, vol. 27, No. 18, 1988, pp. 3069–3075.

*Primary Examiner*—Asok Pal
*Assistant Examiner*—P. Achutamurthy
*Attorney, Agent, or Firm*—Edward L. Bowman

[57] ABSTRACT

New fluorenyl silane compounds and method for their production are disclosed. The fluorenyl compounds have the formula

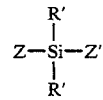

wherein Z is a substituted or unsubstituted fluorenyl radical and Z' is a substituted or unsubstituted cyclopentadienyl-type radical or a halogen.

34 Claims, No Drawings

CYCLOPENTADIENE TYPE COMPOUNDS AND METHOD FOR MAKING

This application is a continuation-in-part of application Ser. No. 07/697,363, filed May 7, 1991, now U.S. Pat. No. 5,191,132. The present invention relates to cyclopentadiene-type compounds. In another aspect this invention relates to methods for making cyclopentadiene-type compounds.

BACKGROUND OF THE INVENTION

The term "cyclopentadiene" as used herein refers to the compound having the formula

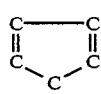

The term "cyclopentadiene-type compounds" as used herein refers to compounds having the cyclopentadiene structure within their structure. Examples include unsubstituted cyclopentadiene, unsubstituted indene, unsubstituted fluorene, and substituted varieties of such compounds. Also included is tetrahydro indene.

Cyclopentadiene-type compounds have found a number of uses in the past. Some such compounds have been found particularly useful for preparing metallocene compounds. Recently, there have been publications which indicate that a wide range of alkyl bridged biscyclopentadienyl compounds are useful as ligands for preparing metallocenes which have utility as catalysts for the polymerization of olefins. Some examples of patents containing such broad disclosures include U.S. Pat. Nos. 4,808,561; 4,794,096; 4,892,851; 4,769,510, and 4,933,403, the disclosures of which are incorporated herein by reference.

While the patents contain broad general statements regarding the effectiveness of a broad genus of compounds, a careful review of the prior art reveals that those statements were based upon the results obtained with only a few of the compounds falling within the patents broad disclosures. Further, the patents do not contain teachings as to how one could make all the compounds which fall within their broad general disclosures. Routes for producing at least some of those compounds falling within the broad teachings of those patents are far from being obvious to one having routine ordinary skill in the art, particularly if one is looking for an economical process for obtaining relatively pure compounds. For example, the only actual example in the patent literature of a bridged cyclopentadienyl-type compound containing a fluorenyl radical appears to be the (cyclopentadienyl) (fluorenyl)-dimethyl methane referred to as isopropyl (cyclopentadienyl) fluorenyl in U.S. Pat. No. 4,892,851. That patent is not considered to disclose how one could make compounds in which a cyclopentadienyl and a fluorenyl radical were bridged by bridging groups other than dimethyl methane.

U.S. Pat. No. 3,426,069 discloses a method for making what is stated to be bis(9-fluorenyl) straight chain alkenes having a straight chain bridge of at least 2 carbon atoms by reacting fluorene with a diol in the presence of an alkali metal hydroxide. The process involves extreme reaction conditions and still provides a yield of only about 20% based on the moles of fluorene reacted.

One object of the present invention is to provide new methods for preparing certain cyclopentadiene-type compounds.

Another object is to provide methods which can provide increased yield of the desired cyclopentadiene-type compounds.

Another object is to provide methods which can produce cyclopentadienyl-type compounds that are more readily obtained in substantially pure form.

Still another object is to provide certain new cyclopentadienyl-type compounds.

Other aspects, objects, and advantages for the present invention in its various embodiments will become apparent to those skilled in the art from the disclosure which follows:

SUMMARY OF THE INVENTION

The present invention provides processes for preparing compounds of the formula Z-R-Z wherein R is a structural bridge between the two Z's, each Z can be selected from cyclopentadienyl-type radicals such as substituted or unsubstituted cyclopentadienyl, indenyl, fluorenyl, or tetrahydro indenyl or the like or one is such a cyclopentadienyl-type radical and the other is a halogen or the like, i.e. a pseudohalogen, —CN, azide. In accordance with one embodiment of the compound, wherein the Z radicals are the same and are both organic, are prepared by reacting the specific Z precursor with a suitable precursor for R. In accordance with another embodiment, compounds in which one Z radical is organic and one is a halogen or the like are produced by reacting the selected Z precursor with a dihalo precursor compound under suitable conditions. In accordance with yet another embodiment of the present invention there is provided a method for preparing compounds of the formula Z—CH$_2$—Z' wherein Z and Z' are organic and different and Z is an unsubstituted fluorenyl or substituted fluorenyl and Z' is a unsubstituted cyclopentadienyl, substituted cyclopentadienyl, unsubstituted indenyl, substituted indenyl, tetrahydroindenyl, unsubstituted fluorenyl, or substituted fluorenyl. In accordance with another embodiment there is provided a process comprising reacting a compound of the formula Z—Me(alkyl)$_3$, wherein Me is Si, Ge, or Sn and where Z is a substituted or unsubstituted fluorenyl with an alkali metal alkyl to form the alkali metal salt of Z—Me(alkyl)$_3$ and then reacting said alkali metal salt with a dihalomethane to produce 9-methyl halide-9-trialkyl Me Z, and reacting that compound with the alkali metal salt of Z' to yield Z—CH$_2$Z'.

Also in accordance with the present invention there are provided a number of new cyclopentadienyl compounds including those of the formula Z-R-Z wherein at least one Z is a substituted or unsubstituted fluorenyl and R is a bridge comprising an alkylene radical, Sn, Si, Ge, B, Al, N, P or O.

DETAILED DESCRIPTION OF THE INVENTION

In accordance with one aspect of the present invention, compounds of the formula Z-R-Z wherein at least one Z is selected from the group consisting of an organic radical having cyclopentadienyl functionality and the other Z is selected from the same organic radical or a halogen selected from fluorine, chlorine, bromine, or iodine can be prepared by reacting the precursor for the organic radical Z with an alkali metal alkyl under suitable reaction conditions to produce the corresponding Z anion. The resulting Z anion is then contacted under suitable reaction conditions with a suitable compound of the formula X-R-X wherein each X is individually selected from Fl, Br, Cl, or I and R is an alkylene radical having 1 to 20 carbon atoms, said alkylene radical optionally having in the alkylene chain an element selected from Ge, Si, B, N, Al, Sn, P and O. The phrase "in the alkylene chain" as used herein refers to the main chain as distinguished from branches on the chain. Alternatively, instead of an alkylene chain, R can be any suitable bridging unit derived from a compound which reacts like a dihaloalkylene compound in the inventive process. Examples would include dihalo compounds of Ge, Si, B, Al, P, Sn and the like.

A particularly preferred type of dihalo compounds are those of the formula

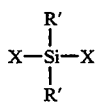

wherein each R' is individually selected from hydrogen or an organo radical containing 1 to 40 carbon atoms and each X is individually selected from Cl, Br, or I. The currently most preferred such dihalo silane compounds are the organo dihalo silanes. In such compounds preferably at least one of the R' groups is a $C_1$-$C_{10}$ alkyl group, a $C_1$-$C_{10}$ fluoroalkyl group, a $C_6$-$C_{10}$ aryl group, a $C_6$-$C_{10}$ fluoroaryl group, a $C_1$-$C_{10}$ alkoxy group, a $C_2$-$C_{10}$ alkenyl group, a $C_7$-$C_4$ arylalkyl group, a $C_8$-$C_{40}$ arylalkenyl group, or a $C_7$-$C_{40}$ alkylaryl group. It is also within the scope of the invention for R' and R' to be joined to form a heterocyclic ring containing Si.

The precursor for the organic radical Z can be selected from unsubstituted cyclopentadiene, substituted cyclopentadiene, unsubstituted indene, substituted indene, unsubstituted fluorene, substituted fluorene, tetrahydroindene and cyclopentadienyl compounds having additional condensed saturated or unsaturated ring systems with or without heteroatoms such as N, P, Si, O, and Sn in the ring system. The currently preferred Z is a hydrocarbyl organic compound.

The term "fluorene" as used herein refers to the tricyclic compounds which is generally illustrated by the following structural formula:

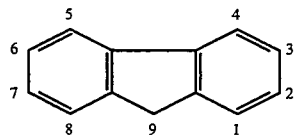

In the chemical names used herein, the position of substituents on the fluorene will be indicated by referring to the point of attachment on the ring carbon by the number system illustrated in the above formula. Unless otherwise indicated the term "fluorenyl" as used herein refers to the 9-fluorenyl radical.

The substituents on the organic radical Z or the precursor to the organic radical Z can vary over a wide range and can be basically any substituent which does not interfere with the method of the present invention. Currently preferred embodiments employ precursors in which the organic radical Z is hydrocarbyl. Typical substituents on substituted hydrocarbyl Z radicals include alkyl substituents having 1 to 20 carbon atoms.

Some examples of substituents include methyl, ethyl, propyl, butyl, tert-butyl, phenyl, benzyl, cyclohexyl, and the like. A particularly preferred embodiment employs a Z having 1 to 4 alkyl substituents each having 1 to 5 carbon atoms. It is also within the scope of the present invention to have the Z or Z' component have substituents which join to form another cyclic ring, especially a $C_4$-$C_6$ ring.

The reaction between the precursor for the organic radical Z and the dihaloelkylene compound can be carried out over a wide range of conditions depending upon the results desired. Typically the precursor for the organic radical Z is reacted with an alkali metal alkyl in the presence of a suitable liquid solvent and then the resulting Z anion is reacted with the dihaloelkylene compound in the presence of a suitable liquid solvent.

The alkali metal alkyls employed could include any alkali metal alkyls capable of forming a suitable Z anion. Typically the alkali metals would be selected from sodium, potassium, and lithium and the alkyl would have 1 to 8, more preferably 1 to 4 carbon atoms. Typically the anion would be formed by dissolving the Z compound in a suitable liquid diluent and then adding the alkali metal alkyl. Techniques of forming such anions are known in the art. Typically in the past such techniques have used as the liquid diluent a polar solvent, for example, tetrahydrofuran. The present applicants have found that non-polar solvents such as alkanes, cycloalkanes, aromatic hydrocarbons and ethers can also be employed. Some specific examples include toluene, hexane, and diethylether.

After the substituted or unsubstituted Z ion has been obtained, it is reacted with the dihaloalkylene compound. The resulting product can then be washed with an aqueous saturated ammonium chloride solution, washed with water, and then the organic phase recovered. The product can be purified by washing with a suitable liquid, by dissolving the product, and recrystallizing the product.

The liquid solvent employed can be any suitable liquid. Examples of suitable liquids include diethylether, tetrahydrofuran, hydrocarbons such as pentane, hexane, and toluene, and mixtures thereof. When the inventive process is used to prepare a compound of the formula Z-R-Z wherein one Z is a halide, it has been found desirable to employ a non-polar liquid solvent for the reaction between the Z anion and the dihaloelkylene. Preferably the Z anion is gradually added to a stirred solution of the dihaloalkylene. The product can be recovered and purified in the same manner as described above.

The reaction pressure and temperatures for the processes disclosed herein are not particularly critical and can vary over a wide range depending upon the results desired. Atmospheric pressures are currently preferred although higher or lower pressures could be employed. Typically, the reaction temperatures will be in the range of about $-100°$ C. to about 100 C. Generally it is convenient to carry out the reactions at ambient temperature.

The molar ratio of the Z anion to the dihaloelkylene or equivalent can vary over a wide range depending upon the results desired. When one desires to prepare a compound in which each Z is an organic radical having the same cyclopentadienyl functionality, it is generally preferred that the molar ratio of the Z anion to the dihaloalkylene compound be at least about 2 to 1. In a process wherein a compound of the formula Z-R-X is formed wherein X is fluorine, chlorine, bromine, or iodine, etc., it is generally preferred that the molar ratio of the organic Z anion to the dihaloalkylene compound be no greater than about 1 to 1.

It is also within the scope of the present invention to prepare the Z anion in a polar liquid solvent such as tetrahydrofuran and then to separate substantially all of the tetrahydrofuran from the alkali metal Z salt and then to add that solid alkali metal Z salt to a mixture of the dihaloalkylene compound in a non-polar liquid.

In the formation and reaction of the Z anion in the reactions disclosed herein, it can be desirable to conduct such in the presence of compounds such as hexamethyl phosphoric triamide, propylene carbonate, or the like. When used such compounds are generally used in an amount sufficient to improve either the yield or the speed of the reaction. Propylene carbonate is particularly favored for use with cyclopentadienyl sodium. Hexamethyl phosphoric triamide is particularly favored with cyclopentadienyl lithium.

Preparation of Unsymmetrical Z-R-Z' Compounds

In accordance with this aspect of the invention, compounds are produced of the formula Z-R-Z' wherein Z and Z' are different and are selected from cyclopentadienyl-type compounds. Some preferred examples include substituted fluorenyl, unsubstituted fluorenyl, cyclopentadienyl, substituted cyclopentadienyl, indenyl, substituted indenyl, and tetrahydroindenyl.

One of the processes for preparing unsymmetrical Z-R-Z' compound involves reacting the Z alkyl halide of the formula Z-R-X with the alkali metal salt of the selected Z' compound. The compound Z-R-Z' can be produced by combining the Z alkyl halide and the Z' anion in solution. The liquid diluent used in forming those solutions can be any suitable liquid, examples include those liquids named above as suitable for forming the symmetrical compounds Z-R-Z, with or without polar additives such as propylene carbonate, hexamethyl phosphoric triamide, etc. The resulting product can be recovered and purified using techniques of the type mentioned above for the symmetrical compounds.

It has been noted that when Z is a fluorenyl radical; substituted or unsubstituted; R is a methylene radical; and Z' is an unsubstituted cyclopentadienyl, there is a preferred method for preparing such fluorene-$(CH_2)$-cyclopentadiene compounds. Specifically, such compounds are prepared by reacting an alkali metal alkyl with the selected substituted or unsubstituted fluorene compound to obtain a solution of the selected fluorenyl anion. The solution of the anion is combined with halotri(alkyl or aryl) Me, where Me is Si, Ge, or Sn to produce the corresponding (9-tri(alkyl or aryl) Me) fluorene compound. This compound can then be dissolved in a suitable liquid and reacted with an alkali metal alkyl. The resulting salt is then added as a solid or in solution gradually to a solution of dihalomethane. Preferably, the molar ratio of the dihalomethane to the silyl-fluorenyl anion is generally at least about 1 to 1, more preferably greater than 2 to 1. The resulting (9-tri-(alkyl or aryl) Me) (9-methylchloride) fluorene compound can then be recovered and reacted with a solution of the alkali metal anion of the selected Z' compound. The ratio of the Z' anion to the fluorene compound can vary over a wide range. It is currently preferred that the ratio be at least about 1/1, more preferably 2/1. The resulting product can be recovered and purified as described previously. This process will also work where Z' is another cyclopentadienyl-type compound such as substituted cyclopentadienyl, unsubstituted indenyl, substituted indenyl, tetrahydroindenyl, substituted fluorenyl, or unsubstituted fluorenyl, and the like and Z is either substituted or unsubstituted fluorenyl, and Z and Z' are different.

Illustrative examples of specific methods for preparing specific substituted fluorenyl compounds are provided in the following examples.

A further understanding of the present invention will be provided by the following examples of some specific embodiments of the present invention.

EXAMPLE I

Preparation of 1-methyl fluorene

Two different reaction schemes have been used to prepare 1-methyl fluorene from fluoranthene. The reaction schemes can be illustrated by the following flow diagram. Both schemes involve the use of 1-carboxylic acid fluorenone as a starting material.

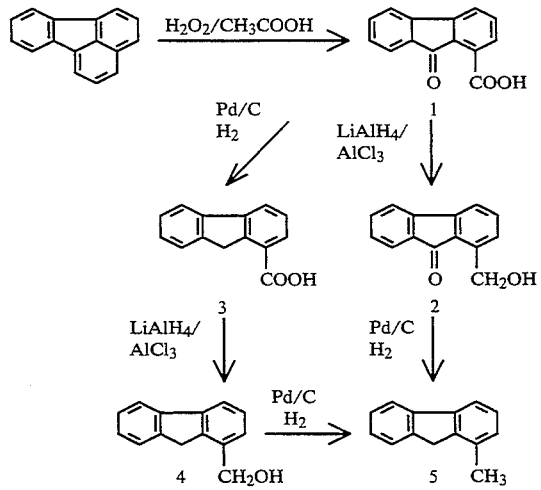

To prepare the 1-carboxylic acid fluorenone, i.e. formula 1, 20.2 g (0.1 m) of fluoranthene was dissolved in 150 ml of acetic acid at 90° C. At that temperature 200 ml of 30% aqueous $H_2O_2$, was then added gradually. Then the reaction mixture was stirred for another 3 hours at that temperature. At the beginning of the reaction, a light yellow precipitate was formed that disappeared after some time. Then the reaction mixture was cooled to 0° C. in an ice bath. An orange precipitate was formed and filtered off. The filtrate was poured into cold diluted aqueous HCl. An orange yellow precipitate was formed which was washed twice with $H_2O$ and then dissolved in an aqueous $NH_3$ solution in order to remove the unreacted fluoranthene. Then the mixture was filtered. When the filtrate was neutralized with HCl, an orange precipitate was formed. The precipitate, 1-carboxylic acid fluorenone, was filtered off and dried. The amount produced was 13.4 g.

Scheme I

About 0.76 g (0.02 mmol) of $LiAlH_4$ was suspended in a mixture of 75 ml of diethylether and 25 ml of tetrahydrofuran (dried over $LiAlH_4$). The mixture was cooled to 0° C. in an ice bath. Then 1.35 g (0.01 mmol) of $AlCl_3$ was added in small portions and the mixture was stirred at room temperature for 15 min. Then 4.2 g (0.02 mmol) of the carboxylic acid fluorenone dissolved in 400 ml of tetrahydrofuran was added via a dropping funnel while the reaction mixture was heated to reflux. Stirring was maintained for an additional 30 min. Then the reaction mixture was cooled to room temperature and the unreacted $LiAlH_4$ was destroyed with an aqueous solution of HCl. The organic phase was removed in vacuo. The solid, i.e. 1-hydroxymethyl fluorenone (formula 2), was recovered in the amount of 3.2 g. The raw 1-hydroxymethyl fluorenone can be used without further purification. 2 g of palladium on carbon catalyst containing about 10 weight percent Pd was weighed into a flask and 4.2 g (0.02 mmol) of the recovered 1-methanol fluorenone was dissolved in 250 ml tetrahydrofuran and added to the flask. The hydrogenation was conducted at room temperature with a slight overpressure of $H_2$ until 1350 ml of $H_2$ was consumed. The reaction mixture was filtered and the solvent of the filtrate was removed in vacuo. The creme colored residue was extracted with pentane, the solution was filtered over silica, and the solvent removed in vacuo. The resulting product, 1-methyl fluorene, was a colorless solid and formed in quantitative yield.

Scheme II

In the second route, the 1-carboxylic acid fluorenone is reduced using the palladium carbon catalyst in the same manner as described for converting the 1-hydroxymethyl fluorenone to 1-methyl fluorene. A quantitative yield of 1-carboxylic acid fluorene, i.e. formula 3, was obtained. The volume of hydrogen consumed was 960 ml. This product was then reduced to 1-hydroxymethyl fluorene, i.e. formula 4, by using the $LiAlH_4$ and $AlCl_3$ as described for the production of the 1-hydroxymethyl fluorenone. The 1-hydroxymethyl fluorene was then reduced using the palladium carbon catalyst and hydrogen to yield 1-methyl fluorene.

EXAMPLE II

Preparation of 1-tert-butyl fluorene

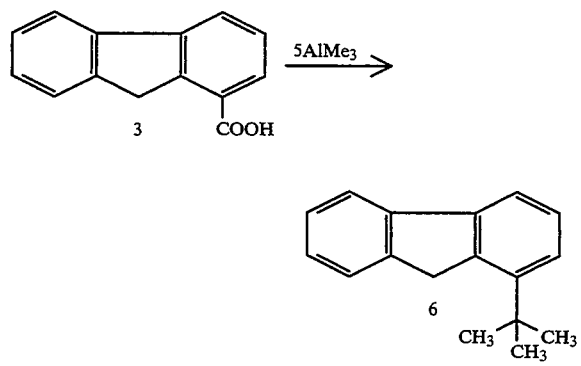

About 2 g (0.01 mmol) of 1-carboxylic acid fluorene was suspended in 50 ml of toluene. Then 4.6 ml $AlMe_3$ was added to the solution and the reaction mixture was refluxed for 10 hours. Upon heating, the reaction mixture formed a homogeneous solution. The reaction mixture was cooled to room temperature and then poured into ice cooled diluted aqueous HCl. The organic layer was separated, washed with $H_2O$, and dried over $Na_2SO_4$. Then the solvent was removed in vacuo. The colorless residue was extracted with pentane, the solution filtered over silica, and the solvent removed in vacuo. The yield of 1-tert-butyl fluorene, formula 6, was quantitative.

EXAMPLE III

Preparation of 2-ethyl fluorene

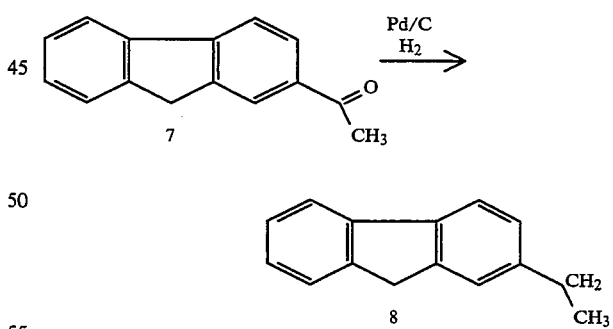

In this reaction, 2-acetyl fluorene, i.e. formula 7, was converted into 2-ethyl fluorene by hydrogenation. The hydrogenation reaction was analogous to the reaction used to convert the compound of formula 6 to the compound of formula 5. The $H_2$ volume used was 970 ml. After the removal of the solvent in vacuo, a creme colored solid was obtained. It was dissolved in pentane and the solution was filtered over silica. Pentane was removed in vacuo. The yield of 2-ethyl fluorene was quantitative.

EXAMPLE IV

Preparation of 2-tert-butyl fluorene

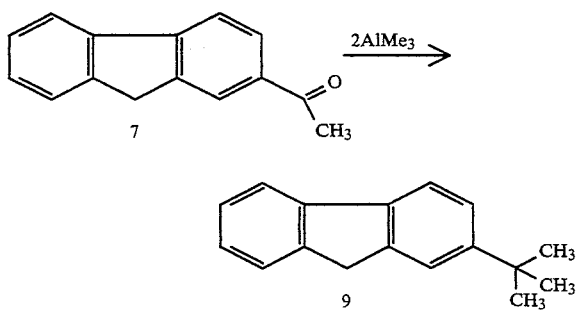

In the reaction 2-acetyl fluorene was reacted with trimethyl aluminum. The methylation was analogous to the conversion of compound 3 to compound 6 described in Example II. However, in this case, only a two-fold excess of AlMe$_3$ was necessary. The 2-tert-butyl fluorene was formed as a white solid in quantitative yield.

EXAMPLE V

Preparation of 4-methyl fluorene

Two different reaction schemes have been used to prepare 4-methyl fluorene, i.e. formula 15. The schemes can be summarized as follows.

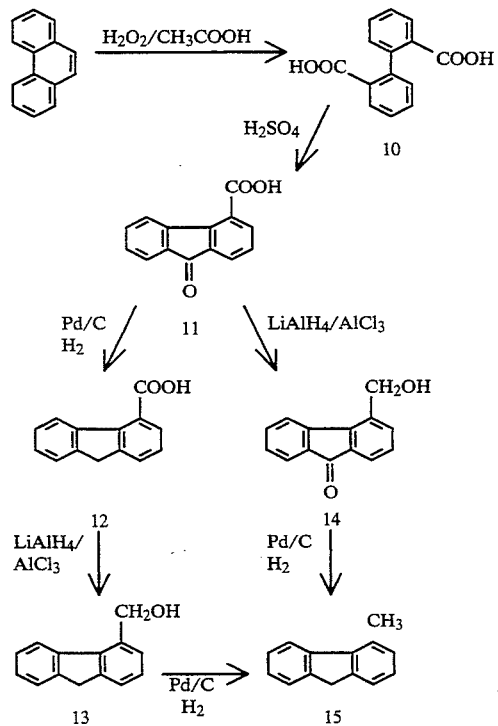

Both schemes require 4-carboxylic acid fluorenone, formula 11, as a starting material. This compound was produced from phenanthrene using a procedure similar to that disclosed in J. Org. Chem. 21, 243 (1956) except that no acetic anhydride was used. Instead, hydrogen peroxide and acetic acid were used to obtain a 67% yield of 2,2'-dicarboxylic acid biphenyl, i.e. formula 10.

The biphenyl product of formula 10 was then oxidized using sulfuric acid in the manner taught in J. Am. Chem. Soc. 64, 2845 (1942) to obtain an 82% yield of 4-carboxylic acid fluorenone, i.e. formula 11.

Scheme 1

The compound of the formula 11 was reduced using LiAlH$_4$ and AlCl$_3$ in the same manner as in Example I. The reaction produced an 80% yield of 4-hydroxymethyl fluorenone, i.e. formula 14, which was then reduced using hydrogen and the paladium carbon catalyst previously described. A quantitative yield of 4-methyl fluorene resulted.

Scheme 2

The compound of formula 11 was reduced using hydrogen and the palladium carbon catalyst described previously. The reaction produced a quantitative yield of 4-carboxylic acid fluorene, i.e. formula 12. Reduction of this acid with LiAlH$_4$ and AlCl$_3$ resulted in an 80% yield of 4-hydroxymethyl fluorene, i.e. formula 13. This product was then reduced using hydrogen and the palladium carbon catalyst to produce a quantitative yield of 4-methyl fluorene.

EXAMPLE VI

Preparation of 4-tert-butyl fluorene 4-carboxylic acid fluorene was reacted with trimethylaluminum generally as described in Example II to produce a 60% yield of 4-tert-butyl fluorene.

EXAMPLE VII

Preparation of 2,7-bis(tert-butyl)-4-methyl fluorene

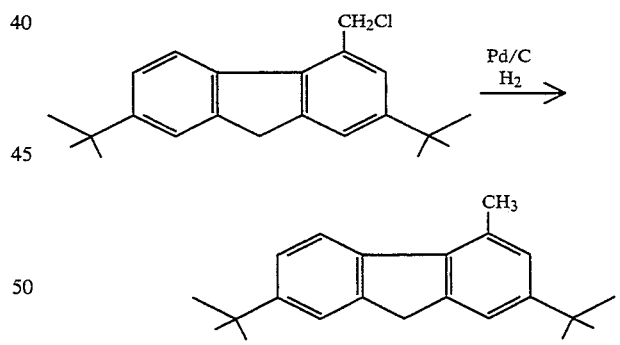

2,7-bis(tert-butyl)-4-methylene chloride fluorene was reduced using hydrogen and the palladium carbon catalyst to obtain a quantitative yield of 2,7-bis(tert-butyl)-4-methyl fluorene.

EXAMPLE VIII

Preparation of 1,2-bis(9-fluorenyl)ethane

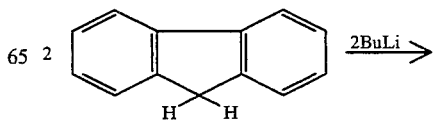

-continued

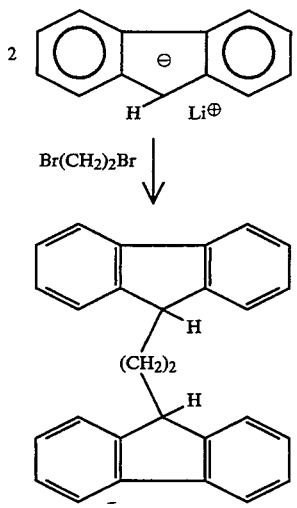

About 8.3 g (0.05 m) of fluorene was dissolved in 150 ml of tetrahydrofuran. Then 31.8 ml (0.05 m) of butyl lithium (1.6 molar in hexane) was added dropwise to this solution. After one hour, 2.3 ml (0.25 m) of dibromoethane in 25 ml of tetrahydrofuran was added. The solution was stirred for 3 hours. The yellow solution was washed with 50 ml of an aqueous $NH_4Cl$ solution (5 g $NH_4Cl$/50 ml $H_2O$), then washed with 50 ml of water and then the organic phase was dried over $Na_2SO_4$. Then the solvent was removed in vacuo. The light yellow residue was washed twice with 25 ml of pentane. The resulting product was white. The yield was 12.5 g, i.e. a yield of about 70%, based on the moles of fluorene reacted. The product was confirmed through $^1H$ NMR, $^{13}C$ NMR, mass spectroscopy, and gas chromatography.

EXAMPLE IX

Preparation of 1-bromo-2-(fluorenyl)ethane

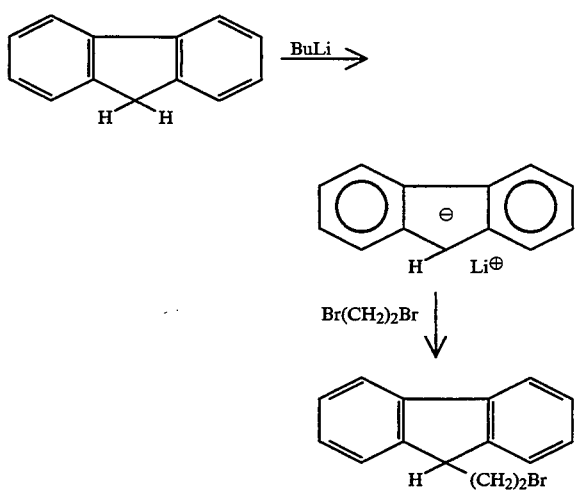

In this reaction, 8.3 g (0.05 m) of fluorene was dissolved in 150 ml of tetrahydrofuran. Then 31.8 ml (0.05 m) of butyl lithium (1.6 molar in hexane) was added dropwise to this solution. After one hour, this solution was added gradually to a stirred solution of 9 ml (0.1 m) of dibromoethane in 300 ml of pentane within 2 hours. Then the reaction mixture was treated with 50 ml of an aqueous $NH_4Cl$ solution, and then washed with 50 ml of water. The organic phase was dried over $Na_2SO_4$. Then the solvent was removed in vacuo. The yellow residue was dissolved in pentane. The pentane solution was filtered over silica. The solution was concentrated to about 20% of the original volume and then the product was crystallized at $-30°$ C. A yield of 10.88 g of 1-bromo-2-(fluorenyl)ethane was obtained. The product was characterized through $^1H$ NMR, $^{13}C$ NMR, and Mass spectroscopy.

EXAMPLE X

Other bromo, fluorenyl alkyl compounds

Reation similar to that set forth in Example IX have been carried out substituting other dihalo alkyls for 1,2-dibromo ethane. Examples of such other dihalo compounds include 1,3-dibromopropane, 1,2-di-bromo-2-methyl ethane, and dichloro methane. The corresponding fluorenyl alkyl halides were obtained.

EXAMPLE XI

Other bis-fluorenyl compounds

Reactions similar to that set forth in Example VIII were carried out by substituting other X-R-X compounds for dibromo ethane. Examples of such other dibromo compounds include 1,3-dibromo propane, dibromo methane, 1,2-di-bromo-2-methyl ethane, and dimethyl dibromo silane, i.e. $BrSi(CH_3)_2Br$. In each case, di-fluorenyl compounds were obtained in which the fluorenyl radicals were connected by the bridge remnant of the dihalo compound.

EXAMPLE XII

Reactions similar to that set forth in Example VIII were carried out by substituting alkyl substituted fluorene compounds for the unsubstituted fluorene. Examples of the substituted fluorenes used included 1-tert butyl fluorene, 1-methyl fluorene, 2-ethyl fluorene, 2-tert butyl fluorene, 4-methyl fluorene, 1-methyl-4-methyl fluorene, 1-tert butyl-4-tert butyl fluorene, 2-tert butyl-7-tert butyl fluorene, 2,7-di-tert-butyl-4-methyl fluorene, and 4-tert butyl fluorene. In each case, a bis(-substituted fluorenyl) alkane was obtained in which the fluorenyl groups corresponded to the respective substituted fluorene compound.

EXAMPLE XIII

Preparation of fluorene $(CH_2)_2$ cyclopentadiene

Cyclopentadiene was reacted with butyllithium in tetrahydrofuran to yield cyclopentadienyl lithium. A solution of 0.02 m cyclopentadienyl lithium in 150 ml of tetrahydrofuran at ($-40°$ C.) and a solution of fluorenyl $(CH_2)_2$ Br in 50 ml of THF were mixed together at room temperature. Then 10 ml of hexamethyl phosphine triamide (HMPT) was added. After three hours stirring at room temperature, this solution was washed with 50 ml of an aqueous $NH_4Cl$ solution, then washed with 50 ml of water, and then the organic phase was dried over $Na_2SO_4$. The solvent was removed in vacuo. The resulting (fluorenyl) ethane (cyclopentadienyl) can be purified by dissolving in pentane and the crystallizing. The product was characterized using mass spectroscopy and gas chromatography.

EXAMPLE XIV

Reactions similar to that described in Example XIII were carried out substituting other fluorenyl bromo alkanes for the fluorenyl bromo ethanes. Examples of the other bromo alkanes used include 1-fluorenyl-3-bromo propane 2,7-di-tert-butyl fluorenyl, and 1-methyl-2-fluorenyl-1-bromo ethane. The corresponding alkyl bridged fluorenyl-cyclopentadienyl compounds were obtained.

EXAMPLE XV

Reactions similar to that described in Examples XIII and XIV were carried out sing either methylcyclopentadiene, substituted fluorene, or indene, instead of cyclopentadiene but without HMPT. Such reactions produced the following compounds: 1-(fluorenyl)-2-(indenyl) ethane, 1-(fluorenyl)-2-(methylcyclopentadienyl) ethane, 1-(fluorenyl)-3-(indenyl) propane, 1-(fluorenyl)-3-(methylcyclopentadienyl) propane, 1-(fluorenyl)-2-(methyl)-2-(indenyl) ethane, and 1-(fluorenyl)-2-(methyl)-2-(methylcyclopentadienyl) ethane, 1-(1-methyl fluorenyl)-2-(4-methyl fluorenyl) ethane, 1-(1-t-butyl fluorenyl)-2-(4-t-butyl fluorenyl ethane, and 1-(2,7-di-tert-butyl fluorenyl)-2-fluorenyl ethane.

EXAMPLE XVI

Preparation of 9-(trimethylsilyl)fluorene

First, 8.3 g (0.05 m) of fluorene was dissolved in 150 ml of tetrahydrofuran. Then 31.8 ml (0.05 m) of butyl lithium (1.6 molar in hexane) was added dropwise to this solution. After a stirring period of one hour, 6.3 ml (0.05 mol) of chlorotrimethylsilane, dissolved in 25 ml of tetrahydrofuran was added to this solution over 3 hours. The reaction mixture was stirred for an additional 3 hours. Then, 50 ml of an aqueous NH$_4$Cl solution was added to the dark yellow solution. The solution was treated with 50 ml of water. The organic phase was dried over Na$_2$SO$_4$. Then the solvent was removed in vacuo. The yellow residue was dissolved in pentane. The product 9-(trimethylsilyl)fluorene was crystallized at 4° C. A yield of 8.33 g was obtained.

EXAMPLE XVII

Preparation of (cyclopentadienyl)(fluorenyl)methane

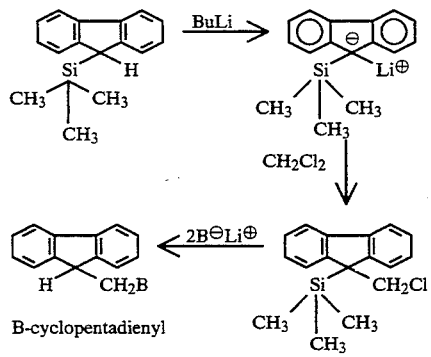

Here, 4.76 g (0.02m) of the 9-(trimethylsilyl)fluorene obtained from the reaction described in Example XVI was dissolved in 150 ml of tetrahydrofuran. Then, 12.5 ml (0.02 m) butyl lithium (1.6 molar in hexane) was added dropwise to the solution. After one hour of stirring at room temperature the solvent was removed and the residue was added gradually to a solution of 5 ml of dichloromethane (0.08 m) in 300 ml pentane. The reaction mixture was stirred for another hour. The yellow solution was filtered and the solvent was removed in vacuo to yield 9-(chloromethyl)-9-(trimethylsilyl) fluorene.

The 9-(chloromethyl)-9-(trimethylsilyl) fluorene was dissolved in 200 ml tetrahydrofuran and added dropwise to a solution of cyclopentadienyl lithium (0.04m) in 200 ml of tetrahydrofuran. The reaction mixture was stirred for another 2 hours. The yellow solution was washed with 50 ml of an aqueous NH$_4$Cl solution, then washed with 50 ml of water, and then the organic phase was dried over Na$_2$SO$_4$. Then the solvent was removed in vacuo. The raw product was dissolved in pentane and was crystallized at −30° C. The recovered product is 1-fluorenyl-1-cyclopentadienyl methane.

EXAMPLE XVIII

Preparation of (cyclopentadienyl)(fluorenyl)methane

Here 4.76 g (0.02 m) of (9-trimethylsilyl)fluorene (melting point: 98° C.) was dissolved in 150 ml of tetrahydrofuran and cooled to −40° C. Then 12.5 ml (0.02 m) butyllithium (1.6 molar in hexane) was added dropwise to the solution. After one hour stirring at room temperature, the solvent was removed in vacuo and the yellow residue was added gradually to a solution of 5 ml of dichloromethane (0.08m) in 500 ml pentane within 30 minutes. The reaction mixture was stirred for another 45 minutes. The yellow solution was filtered (to remove LiCl), concentrated, and cooled down to crystallize the product 9-(trimethylsilyl)-9-(chloromethyl)fluorene.

The raw product had a yellow color (90% G.C. analysis). The crystallized product had a pale yellow color, 75–80% yield, and a melting point of 105°–106° C.

Then 4.3 g (0.015 m) of the pale yellow crystals were added in small portions to a solution of cyclopentadienyllithium (0.03 m) in 200 ml of tetrahydrofuran containing 3 ml of hexamethyl phosphorus triamide. The reaction mixture was stirred for another 30 minutes. The dark solution was washed with 50 ml of an NH$_4$Cl solution, the washed with 50 ml of water and then the organic phase was dried over Na$_2$SO$_4$. Then the solvent was removed in vacuo. The thick oily raw product was dissolved in pentane and crystallized at −30° C. The only side product noted was fluorene which can be recovered for subsequent use. The yield of (cyclopentadienyl)(fluorenyl)methane was 60%. The recrystallized product had a melting point of 85°–86° C.

EXAMPLE XIX

Preparation of (cyclopentadienyl)(fluorenyl)methane

Here 2.9 g (0.01 mol) of (9-chloromethyl)(9-trimethylsilyl) fluorene (raw material from Example XVII) was dissolved in 50 ml of tetrahydrofuran. Then 50 ml of propylene carbonate was added. Then 2.64 g (0.03 mol) of cyclopentadienyl sodium was added. The reaction mixture was stirred over night. Then 100 ml of hexane were added and the reaction mixture was washed three times with 100 ml of water each time. Then the organic layer was separated and dried over Na$_2$SO$_4$. Then the solvent was evaporated in vacuo. The residue was dissolved in toluene, the solution filtered over silica. Then the solvent was removed in vacuo and the residue dried over night at $10^{-3}$ bar. The residue was dissolved in diethylether and the solvent

15 was removed in vacuo at 0° C. The yield of (cyclopentadienyl)(fluorenyl) methane was 90%.

EXAMPLE XX

Preparation of FlSiMe₂Cl

Here 5 g (30 mmol) of fluorene was dissolved in 150 ml of diethyl ether and reacted with 18.8 ml of butyllithium (1.6M in hexane). After stirring for three hours, the solvent was evaporated to yield a yellow powder. Then 5 g of Me₂SiCl₂ (39 mmol) was dissolved in 200 ml of anhydrous pentane and then solid fluorenyl lithium salt was added. After stirring for one hour, the mixture was filtered to remove precipitated lithium chloride. Evaporation of the solvent yielded a yellow oil which was characterized by GC/MS as fluorenyldimethylchlorosilane.

EXAMPLE XXI

Preparation of FlSiMe₂Cp

Here 4.7 g of crude FlMe₂SiCl from Example XX was dissolved in 200 ml of diethyl ether and 2.6 g (30 mmol) of CpNa, i.e. cyclopentadienyl sodium was added. After stirring for 12 hours, the mixture was washed with water to remove NaCl and the organic layer was dried over Na₂SO₄. Evaporation of the solvent yielded an orange oil, characterized by GC/MS as 9-(dimethyl cyclopentadienyl silyl)fluorene, i.e. FlSi(Me)₂Cp, which could also be called 1-(9-fluorenyl)-1-cyclopentadienyl-1,1-dimethyl silane.

EXAMPLE XXII

Preparation of FlSiPh₂Cl

Here 5 g (30 mmol) fluorene, dissolved in ether, was reacted for three hours with 18.8 ml of butyllithium (1.6M in hexane). The solvent was evaporated to yield yellow fluorenyl lithium. Then 11.4 g (45 mmol) of Ph₂SiCl₂, i.e. diphenyl dichloro silane, was dissolved in 200 ml of pentane and the solid fluorenyl lithium was added in one portion to the pentane solution. After stirring for one hour, the mixture was filtered, the precipitated LiCl was eluated with 50 ml of ether, and the solvent evaporated from the combined organic layers to yield a yellow powder characterized by GC/MS as FlSiPh₂Cl, i.e. fluorenyl-diphenyl chlorosilane. Crystallization in pentane yields colorless crystals of the product, from which a H-NMR-spectra could be obtained.

EXAMPLE XXIII

Preparation of FlSiPh₂Cp

To a solution of 2 g (5 mmol) of the FlSiPh₂Cl of Example XII in 50 ml of diethyl ether and 10 ml of HMPT, 1.2 g (14 mmol) of CpNa was added. The mixture was stirred for 12 hours and then washed with 30 ml water, saturated with CuSO₄ solution, and again washed with water. After drying the organic layer with Na₂SO₄, the solvent was evaporated to yield a white solid, which was characterized by GC/MS as FlCpSiPh₂ accompanied with 10% of bisfluorene.

The use of THF as a solvent in this reaction rather than diethyl ether did not give the desired product. The use of mixtures of THF/propylene carbonate as the solvent results in decomposition of the FluSiPh₂Cl to fluorene.

That which is claimed is:

1. A compound of the formula

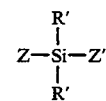

wherein Z is a substituted or unsubstituted fluorenyl; Z' is selected from the group consisting of unsubstituted fluorenyl, substituted fluorenyl, unsubstituted cyclopentadienyl, substituted cyclopentadienyl, unsubstituted indenyl, substituted indenyl, tetrahydroindenyl, and halides; and each R' is individually selected from the group consisting of hydrogen and organo radicals having 1 to 40 carbon atoms further characterized by the fact that if Z' is a halide and each R' is alkyl, then Z is a substituted fluorenyl, and if Z' is not a halide, and both R's are alkyl or phenyl, or one R' is phenyl and the other is fluorenyl and Z is unsubstituted, then Z' is selected from the group consisting of substituted fluorenyl, unsubstituted cyclopentadienyl, substituted cyclopentadienyl, unsubstituted indenyl, and tetrahydroindenyl.

2. A compound of claim 1 wherein each R' is an alkyl radical.

3. A compound according to claim 1 wherein each R' is a methyl radical.

4. A compound according to claim 3 wherein Z' is Cl.

5. A compound according to claim 3 wherein Z is unsubstituted fluorenyl and Z' is unsubstituted cyclopentadienyl.

6. A compound according to claim 3 wherein Z and Z' are identical alkyl substituted fluorenyl radicals.

7. A compound according to claim 1 wherein each R' is a phenyl radical.

8. A compound according to claim 7 wherein Z and Z' are identical alkyl substituted fluorenyl radicals.

9. A compound according to claim 8 wherein Z and Z' are each 1-methylfluorenyl radicals.

10. A compound according to claim 7 wherein Z' is a halide.

11. A compound according to claim 10 wherein Z is an unsubstituted fluorenyl radical.

12. A compound according to claim 11 wherein Z' is Cl.

13. A compound according to claim 7 wherein Z is an unsubstituted fluorenyl radical and Z' is an unsubstituted cyclopentadienyl radical.

14. A compound according to claim 6 wherein Z and Z' are each 1-methyl fluorenyl radicals.

15. A compound according to claim 4 wherein Z is 2,7-di-t-butylfluorenyl.

16. A compound according to claim 10 wherein Z is 2,7-di-t-butylfluorenyl.

17. A compound according to claim 3 wherein Z and Z' are 2,7-di-t-butylfluorenyl.

18. A compound according to claim 1 wherein Z is 2,7-di-t-butylfluorenyl and Z' is unsubstituted cyclopentadienyl.

19. A compound according to claim 18 wherein each R' is methyl.

20. A compound according to claim 18 wherein each R' is phenyl.

21. A compound according to claim 1 wherein Z is 2,7-di-t-butylfluorenyl and Z' is unsubstituted fluorenyl.

22. A compound according to claim 20 wherein each R' is methyl.

23. A compound according to claim 20 wherein each R' is phenyl.

24. A compound according to claim 1 wherein Z and Z' are different and Z' is not a halide.

25. A method for preparing a compound of the formula

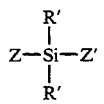

wherein each Z is the same substituted or unsubstituted fluorenyl radical and each R' is individually selected from the group consisting of hydrogen and organo radicals containing 1 to 40 carbon atoms, comprising reacting the precursor for the Z fluorenyl radical with an alkali metal alkyl under suitable conditions to produce the corresponding Z anion and contacting said Z anion under suitable conditions with a dihalosilane of the formula

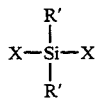

wherein each X is individually selected from Br, Cl, or I and R' is as defined above, said suitable conditions including limiting the solvents employed to non-polar solvents.

26. A method according to claim 25 wherein the molar ratio of the Z anion to the dihalosilane is at least about 2/1.

27. A method according to claim 26 wherein each R' is a methyl radical.

28. A method according to claim 27 wherein each Z is an unsubstituted fluorenyl radical.

29. A method according to claim 27 wherein each Z is a 1-alkyl substituted fluorenyl radical, said alkyl substituent having 1 to 5 carbon atoms.

30. A method according to claim 29 wherein each Z is 1-methyl fluorenyl.

31. A method according to claim 26 wherein each R is a phenyl radical.

32. A method according to claim 31 wherein each Z is 1-methyl fluorenyl.

33. A method according to claim 25 wherein said non-polar solvents are selected from straight chain ethers, alkanes, cycloalkanes, and aromatic hydrocarbons.

34. A method according to claim 33 wherein said non-polar solvent consists essentially of an alkane or mixtures of alkanes.

* * * * *

UNITED STATES PATENT AND TRADEMARK OFFICE
CERTIFICATE OF CORRECTION

PATENT NO. : 5,393,911

DATED : February 28, 1995

INVENTOR(S) : Konstantinos Patsidis et al

It is certified that error appears in the above-identified patent and that said Letters Patent is hereby corrected as shown below:

Column 16, claim 22, line 67, delete "20" and insert therefor ---21---.

Column 17, claim 23, line 1, please delete "20" and insert therefor ---21---.

Column 17, line 2 of the formula, please delete "Z' " and insert therefor ---Z---.

Signed and Sealed this

Twenty-fifth Day of April, 1995

*Attest:*

BRUCE LEHMAN

*Attesting Officer*      Commissioner of Patents and Trademarks